(12) United States Patent
Rogoff et al.

(10) Patent No.: US 6,599,882 B1
(45) Date of Patent: Jul. 29, 2003

(54) SECRETIN AND SECRETIN PHARMACEUTICALS FOR TREATING LACTOSE INTOLERANCE

(76) Inventors: Joseph A. Rogoff, 12812 Panorama View, Santa Ana, CA (US) 92705; F. Jack Warner, 442 Pebble Beach Pl., Fullerton, CA (US) 92835

( * ) Notice: Subject to any disclaimer, the term of this patent is extended or adjusted under 35 U.S.C. 154(b) by 126 days.

(21) Appl. No.: 09/704,553

(22) Filed: Nov. 3, 2000

Related U.S. Application Data

(60) Provisional application No. 60/163,884, filed on Nov. 5, 1999.

(51) Int. Cl.⁷ .............................................. A61K 38/22
(52) U.S. Cl. ........................................................ 514/12
(58) Field of Search ............................................ 514/12

(56) References Cited

U.S. PATENT DOCUMENTS

| | | | |
|---|---|---|---|
| 5,952,301 A | 9/1999 | Druker | 514/12 |
| 5,972,369 A * | 10/1999 | Roorda et al. | 424/424 |
| 6,020,310 A | 2/2000 | Beck | 514/12 |
| 6,020,314 A | 2/2000 | McMichael | 514/21 |

OTHER PUBLICATIONS

Bereza, N.M., Vrachebnoe Delo (12) 79–82 (Dec., 1978) (abstract).*

Dairy Care Press Releases from Oct. 6, 1998 and Oct. 28, 1998.

* cited by examiner

*Primary Examiner*—Phyllis G. Spivack
(74) *Attorney, Agent, or Firm*—Trojan Law Offices

(57) ABSTRACT

A method for treating lactose intolerance wherein the hormone secretin, or an acceptable pharmaceutical synthetic thereof, is administered to a person suffering from lactose intolerance. Patients so treated exhibit greatly improved digestion of lactose.

10 Claims, No Drawings

SECRETIN AND SECRETIN PHARMACEUTICALS FOR TREATING LACTOSE INTOLERANCE

RELATED PATENT APPLICATIONS

This application claims priority to a provisional application Serial No. 60/163,884, filed Nov. 05, 1999.

BACKGROUND OF THE INVENTION

1. Field of the Invention

The invention relates to a pharmaceutical and a method for treating lactose intolerance. More particularly, the invention relates to the use of the hormone secretin, or an acceptable pharmaceutical synthetic thereof, in the treatment of lactose intolerance.

2. Description of the Background

Lactose intolerance is the inability to properly digest lactose, the predominant sugar of milk. Lactose is also known as milk sugar. Symptoms of lactose intolerance include abdominal bloating, gaseousness, cramping and diarrhea following the consumption of food containing dairy products or by-products (such as whey).

Lactose is a disaccharide composed of glucose and galactose. People who are lactose intolerant do not produce enough lactase, an enzyme normally produced by the epithelial cells that line the small intestine, to break down the lactose so it can be absorbed into the bloodstream. When insufficient amounts of lactase are produced, lactose, passes through the intestines unchanged. Undigested lactose creates an osmotic imbalance which results in less water being reabsorbed by the intestinal lining. It also encourages rapid growth of intestinal bacteria that produce large amounts of gas. Those two factors cause the abdominal bloating, gaseousness, cramping, diarrhea and other symptoms of lactose intolerance, which begin about 30 minutes to 2 hours after eating or drinking foods containing lactose. The severity of symptoms varies depending on the amount of lactose each individual can tolerate. While not all persons deficient in lactase have symptoms, those who do are considered to be lactose intolerant.

Lactose intolerance can be congenital, meaning that one is born lactose intolerant. It can also be the result of disease or certain drug treatments. For most people, though, lactose intolerance is a condition that develops naturally over time. After about the age of 2 years, the body begins to produce less lactase. However, many people may not experience symptoms until they are much older.

Between 30 and 50 million Americans are lactose intolerant. Certain ethnic and racial populations are more widely affected than others. As many as 75 percent of all African-Americans and Native Americans and 90 percent of Asian-Americans are lactose intolerant. An estimated 7.5 million adults have severe lactose intolerance.

Individuals with severe lactose intolerance may not be able to tolerate even the very small amounts of lactose that are contained in prepared foods and other so-called hidden sources of lactose. Although-milk and milk by-products are the only natural sources of lactose, lactose is often added to prepared foods, such as breads and other baked goods, sauces, salad dressings, soups, breakfast cereals, lunch meats, candies and other snack foods. Additionally, some products labeled nondairy, such as powdered coffee creamer and whipped toppings, may include ingredients that are derived from milk and therefore contain lactose. Moreover, lactose is used as the base for more than 20 percent of prescription drugs and about 6 percent of over-the-counter medicines.

One means of alleviating the symptoms of lactose intolerance is to reduce or eliminate lactose from the diet. However, it is difficult to avoid the small amounts of lactose contained in prepared foods and other hidden sources of lactose. Moreover, milk and other dairy products are a major source of nutrients in the American diet. One of the most important of these nutrients is calcium. Calcium is essential for the growth and repair of bones throughout life. In the middle and later years, a shortage of calcium may lead to thin, fragile bones that break easily (a condition called osteoporosis). Moreover, new studies suggest that calcium deficiency may be a cause of high blood pressure, which affects about 50 million Americans. It is also believed that a complete removal of lactose from the diet may have an adverse effect on the normal intestinal flora, which is necessary for proper digestion.

Another method of treating lactose intolerance is through the use of lactase enzyme supplements, which are available without a prescription. One form is a liquid that can be added to milk to reduce the lactose content. A few drops are added to a quart of milk, and after 24 hours in the refrigerator, the lactose content is substantially reduced. Another form is a chewable lactase enzyme tablet that is taken just before or with meals to help digest solid foods and other preparations that contain lactose. Three or more tablets are taken, depending on the individuals ability to digest lactose.

There are a number of drawbacks in using lactase enzyme supplements for treating lactose intolerance. First, the supplements must always be on hand when lactose containing foods or other preparations are consumed. Secondly, since there are many hidden sources of lactose, it is often difficult to determine whether any given prepared food item or other preparation contains lactose. Additionally, persons using the enzyme tablets sometimes find that they develop a resistance to the enzyme supplements over a period of use, and consequently they need to take more tablets for the enzymes to be effective.

No treatment method currently exists that improves the body's ability to produce lactase. Therefore, there is a need for a method that is effective in treating lactose intolerance by improving the body's ability to produce the lactase enzyme.

The invention involves a method for treating lactose intolerance wherein the hormone secretin, or an acceptable pharmaceutical synthetic thereof, is administered to a person suffering from lactose intolerance. Secretin is a polypeptide hormone containing 27 amino acids. It is produced by the endocrine cells of the upper small intestine. Secretin, gastrin and cholecystokinin are the 3 major hormones that control human digestion. It is generally believed that the primary action of secretin is to increase the volume and bicarbonate content of secreted pancreatic juices. Secretin is released when acid chyme with pH less than 4.5 to 5.0 enters the duodenum from the stomach. When released, secretin stimulates the pancreas to emit digestive fluids that are rich in bicarbonate, which neutralizes the acidity of the intestines. It is believed that secretin also stimulates the liver to produce bile and stimulates the stomach to produce pepsin, an enzyme that aids the digestion of protein.

Secretin has been proven effective in diagnosing (as opposed to treating) impaired pancreatic function. The US Food and Drug Administration (FDA) has approved porcine secretin, extracted from the duodenum of pigs, for single dose use in diagnosing pancreatic disorders. For these purposes, porcine derived secretin is administered by intravenous infusion during upper gastrointestinal endoscopy or other tests.

SUMMARY OF THE INVENTION

It is the object of the invention to provide a new drug and method which is effective in the treatment of lactose intolerance. In In accordance with the invention, the hormone secretin, or an acceptable pharmaceutical synthetic thereof, is administered to patients suffering from lactose intolerance. It has been discovered by the inventors that the administration of this endogenous substance as a pharmaceutical for the treatment of lactose intolerance leads to a dramatic improvement in the body's ability to produce the lactase enzyme without any adverse side-effects. In so treating patients suffering from lactose intolerance, an elimination of its symptoms, including but not limited to abdominal bloating, gaseousness, cramping and diarrhea following the consumption of food containing dairy products or by-products, is achieved.

The invention provides the only treatment method for lactose intolerance that improves the body's ability to produce the lactase enzyme. With this treatment method, patients will not need to reduce or eliminate their intake of dairy or other lactose containing products. Additionally, patients need only undergo treatment on a one time or periodic basis, and will not need to ingest tablets or take other precautions each time dairy or other lactose containing products are consumed.

DETAILED DESCRIPTION OF THE INVENTION

In accordance with the invention, the hormone secretin, or an acceptable pharmaceutical synthetic thereof, is administered to an individual with lactose intolerance. The secretin, or an acceptable pharmaceutical synthetic thereof, is administered intravenously over a period of about 1 to 4 minutes at a dose of 1 CU (clinical unit) of pharmaceutically acceptable secretin per kilogram of body weight. The intravenous infusion is accomplished by attaching a winged infusion set, otherwise known as a "butterfly needle," to a syringe containing the secret in dosage, and by inserting the needle into the vein, in the arm. The dosage is then pushed through the syringe into the bloodstream over a period of about 1 to 4 minutes.

The inventors' preferred method for performing the intravenous infusion is to first push about 1 ml of the secretin solution into the bloodstream and then to wait 1 minute to make sure the patient is not experiencing any adverse reactions, such as the breakout of a rash or difficulty in breathing. The remainder of the solution is then pushed into the bloodstream over a period of about 2 minutes to about 3 minutes.

To date, the inventors have used porcine derived secretin in the employment of the invention. Synthetic versions of human and porcine secretin may soon be available, and it is intended that the scope of the invention would include pharmaceutically acceptable synthetics of human and porcine secretion, once developed. The scope of the invention is also intended to cover the hormone secretin derived from other mammals, and acceptable pharmaceutical synthetics thereof, if the composition of the secretin from those sources are found to be substantially the same as human or porcine secretin.

In all cases, pharmaceutically acceptable, solutions of the secretin hormone, or synthetics thereof, should be used. The particular solution employed by the inventors consists of porcine secretin manufactured by Ferring AB, which contains. 75 CU of lyophilized, sterile purified secretin, 1 mg of L-cysteine hydrochloride and 20 mg of mannitol per vial. The Ferring AB product comes in a powdered form, and will need to be reconstituted prior to infusion by dissolving the contents of each vial in 7.5 ml of Sodium. Chloride Injection USP, to yield a concentration of 10 CU per ml.

Lactose intolerant individuals treated as described above with a one-time infusion of secretion have been able to consume all dairy and other lactose containing products and preparations over a prolonged period of time without experiencing any of the symptoms of lactose intolerance. This indicates that the invention is effective for treating lactose intolerance by dramatically improving the body's ability to produce the lactase enzyme. The patients so treated did not experience any adverse side-effects from the infusion.

One severely lactose intolerant individual treated with the invention started experiencing some slight symptoms of lactose intolerance about 3 months after receiving the infusion. This suggests that for the severely lactose intolerant individual the treatment may need to be repeated every 3 to 5 months.

The infusion method described above is the best mode currently know by the inventors for implementing the invention. Other possible methods for administering the secretin hormone, or a synthetic thereof, may be developed which may prove effective in implementing the invention, including, without limitation, sublingual administration (drops under the tongue) and transdermal administration (such as using a skin patch).

METHOD OF ACTION

Without intending to be bound by any theory, it is believed that the mechanism of action in treating patients with lactose intolerance centers around the faculty of the hormone secretin, or an acceptable pharmaceutical synthetic thereof, to improve the body's ability to produce the lactase enzyme by activating certain digestive or metabolic processes that are dormant to some degree in the lactose intolerant individual.

The lactose intolerant individual does not produce enough of the lactase enzyme to properly digest lactose (or milk sugar) so that it can be absorbed by the small intestine. The lactase enzyme is normally produced by the epithelial cells of the small intestine. As discussed above, patients receiving a one-time infusion of the hormone secretin have been able to consume dairy and other lactose containing product's long after the treatment without experiencing the symptoms associated with lactose intolerance, thereby exhibiting a dramatic improvement in the body's ability to produce the lactase enzyme.

It is not likely that the one-time inundation of the pancreas with the secretin hormone is sufficient, in and of itself, to effect the long term improvement in the body's ability to produce the lactase enzyme. It appears more likely that the infusion of significant quantities of secretin into the bloodstream serves to activate certain digestive or metabolic processes that lay dormant to some degree in the lactose intolerant individual, and that these enlivened processes are responsible for stimulating, either directly or indirectly, the production of the lactase enzyme by the epithelial intestinal cells. Because the previously dormant digestive or metabolic processes have been awakened, the body's enhanced ability to produce the lactase enzyme continues long after the infusion has been administered.

We claim:

1. A method for treating a patient diagnosed with lactose intolerance comprising an administration of about 1 Clinical Unit per kilogram of body weight of secretin to the patient to allow said patient to remain free from symptoms associated with lactose intolerance for at least three months.

2. The method of claim 1 wherein the secretin is administered by means selected from the group consisting of intravenous, sublingual, and transdermal.

3. The Method of claim 1 wherein the secretin is administered over a period of about 1 to 4 minutes.

4. The Method of claim 1 wherein a first 1 ml of secretin is administered over a period of about 1 minute, a pause of a period of about 1 minute is taken to observe for side, effects, and the remainder of the secretin is administered over a period of about 2 minutes to about 3 minutes.

5. The method of claim 4 wherein the administration of secretin is repeated periodically as clinically necessary.

6. A method for treating a patient diagnosed with lactose intolerance comprising an administration of about 1 Clinical Unit per kilogram of body weight of a pharmaceutical synthetic of secretin to the patient to allow said patient to remain free from symptoms associated with lactose intolerance for at least three months.

7. The method of claim 6, wherein the secretin is administered by means selected from the group consisting of intravenous, sublingual, and transdermal.

8. The Method of claim 6 wherein the secretin is administered over a period of about 1 to 4 minutes.

9. The Method of claim 6 wherein the first 1 ml of secretin is administered over a period of about 1 minute, a pause of a period of about 1 minute is taken to observe for side effects, and the remainder of the secretin is administered over a period of about 2 minutes to about 3 minutes.

10. The method of claim 9 wherein the administration of secretin is repeated periodically as clinically necessary.

\* \* \* \* \*